United States Patent
Vallee et al.

(10) Patent No.: US 9,943,240 B2
(45) Date of Patent: Apr. 17, 2018

(54) NON-INVASIVE METHOD FOR MEASURING TISSUE PERFUSION STATE

(71) Applicant: ASSISTANCE PUBLIQUE—HOPITAUX DE PARIS, Paris (FR)

(72) Inventors: Fabrice Vallee, Paris (FR); Joaquim Mateo, Paris (FR); Didier Payen De La Garanderie, Paris (FR)

(73) Assignee: Assistance Publique—Hopitaux de Paris, Paris (FR)

( * ) Notice: Subject to any disclaimer, the term of this patent is extended or adjusted under 35 U.S.C. 154(b) by 132 days.

(21) Appl. No.: 14/766,098

(22) PCT Filed: Feb. 5, 2014

(86) PCT No.: PCT/IB2014/058815
§ 371 (c)(1),
(2) Date: Aug. 5, 2015

(87) PCT Pub. No.: WO2014/122597
PCT Pub. Date: Aug. 14, 2014

(65) Prior Publication Data
US 2015/0374241 A1   Dec. 31, 2015

(30) Foreign Application Priority Data

Feb. 5, 2013   (FR) .................... 13 50985

(51) Int. Cl.
*A61B 5/026*   (2006.01)
*A61B 5/145*   (2006.01)
(Continued)

(52) U.S. Cl.
CPC ............ *A61B 5/026* (2013.01); *A61B 5/1477* (2013.01); *A61B 5/1491* (2013.01);
(Continued)

(58) Field of Classification Search
CPC . A61B 5/026; A61B 5/14542; A61B 5/14551; A61B 5/1477; A61B 5/1491;
(Continued)

(56) References Cited

U.S. PATENT DOCUMENTS

| | | | | |
|---|---|---|---|---|
| 6,654,622 B1 * | 11/2003 | Eberhard | ........... | A61B 5/14539 600/322 |
| 2006/0259332 A1 * | 11/2006 | Brown | ...................... | B25F 5/00 705/3 |
| 2008/0064942 A1 * | 3/2008 | Gisiger | .............. | A61B 5/14539 600/354 |

FOREIGN PATENT DOCUMENTS

| | | | | |
|---|---|---|---|---|
| WO | WO 2011/024018 | | 3/2011 | |
| WO | WO 2011024018 A1 * | | 3/2011 | ............. A61B 5/026 |
| WO | WO 2011107771 A1 * | | 9/2011 | ......... A61B 5/02007 |

OTHER PUBLICATIONS

Lima AP, Beelen P, Bakker J: Use of a peripheral perfusion index derived from the pulse oximetry signal as a noninvasive indicator of perfusion, Crit Care Med 2002 vol. 30, No. 6, pp. 1210-1213.*
(Continued)

*Primary Examiner* — William Thomson
*Assistant Examiner* — Vynh Huh
(74) *Attorney, Agent, or Firm* — Alston & Bird LLP

(57) ABSTRACT

A non-invasive method for determining the tissue perfusion state in a patient, by measuring the variations in the skin $CO_2$ pressure and in the perfusion index of the patient during the conducting of a localized hyperthermia test.

5 Claims, 8 Drawing Sheets

(51) Int. Cl.
    *A61B 5/1455*    (2006.01)
    *A61B 5/1477*    (2006.01)
    *A61B 5/1491*    (2006.01)
    *A61B 5/00*      (2006.01)

(52) U.S. Cl.
    CPC ...... *A61B 5/14542* (2013.01); *A61B 5/14551* (2013.01); *A61B 5/412* (2013.01); *A61B 5/4884* (2013.01); *A61B 5/6816* (2013.01); *A61B 5/7282* (2013.01)

(58) Field of Classification Search
    CPC ..... A61B 5/412; A61B 5/4884; A61B 5/6816; A61B 5/7282
    USPC .................................................. 600/300, 301
    See application file for complete search history.

(56) References Cited

OTHER PUBLICATIONS

Dres, M., Monnet, X., and Teboul, J.L., "Hemodynamic management of cardiovascular failure by using PCOvenous-arterial difference"; Journal of Clinical Monitoring and Computing, vol. 26, Nr: 5, pp. 367-374; Jul. 25, 2012.
International Search Report and Written Opinion for Application No. PCT/IB2014/058815 dated May 2, 2014.

* cited by examiner

NON-INVASIVE METHOD FOR MEASURING TISSUE PERFUSION STATE

FIELD

The present invention relates to the diagnostic field. More particularly, it relates to a non-invasive method for determining the tissue perfusion state in a patient.

BACKGROUND

States of shock, whatever their origin (cardiogenic, hemorrhagic and/or septic), lead to a drop in tissue perfusion with a more or less marked effect on small vessel perfusion. This microcirculatory impairment leads to a dysfunction or even failure of various organs, which worsens patient prognosis. Currently, there is a need for monitors capable of reflecting the microcirculatory perfusion state. Among the instruments recently developed, some monitors measure tissue $CO_2$ and perfusion index (or PI).

The measurement of the partial $CO_2$ pressure in tissues ($P_{tissue}CO_2$) has been identified as a reliable marker of tissue perfusion in many publications: an increase in tissue $CO_2$, in particular compared with arterial $CO_2$ (calculation of the tissue-arterial gradient: $P_{t-a}CO_2$), reflects tissue accumulation of $CO_2$ due to a concomitant drop in perfusion. The devices currently available for measuring tissue $CO_2$ are gastric tonometry ($P_gCO_2$) or sublingual measurement ($P_{sl}CO_2$). Recently, the measurement of cutaneous $CO_2$ ($P_cCO_2$) at the earlobe has been described as a measurement of tissue $CO_2$ (WO 2011/024018). Like the other measurements of tissue $CO_2$, an elevation in cutaneous $CO_2$ at the earlobe is a marker for poor prognosis in states of shock and a reliable reflection of microcirculatory perfusion.

The perfusion index (PI), derived from the oxygen saturation ($SpO_2$) plethysmography signal, reflects the pulsatile part of the $SpO_2$ signal. This parameter and especially variations therein during the treatment of patients have been described as a reliable reflection of tissue perfusion.

However, the diagnosis of an impairment of microcirculatory perfusion during a state of shock does not make it possible to guide the therapy since these impairments can have various etiologies and therefore require very diverse therapies. Two situations may schematically be encountered:
(1) "Predominant central" problem: due to a generalized hypoperfusion owing to a low cardiac output leading to a macrocirculatory hypoperfusion and therefore also a microcirculatory hypoperfusion (situation encountered in the acute phase of a state of hemorrhagic or cardiogenic shock). In this situation, there is usually no damage to the integrity of the endothelial and microcirculatory function, the peripheral hypoperfusion is due to a drop in overall perfusion. After restoration of central hemodynamics, the microcirculatory hypoperfusion may either rapidly return to normal, or decrease without completely returning to normal due to vasoconstriction of the peripheral territories (such as the skin) favoring perfusion of the noble organs. This case corresponds to a "distributive" problem, due to the abnormality of redistribution from the central blood flow to regional flows, which leads to a residual peripheral hypoperfusion but without structural abnormality of the microvessels and of the endothelial function.
(2) "Predominant peripheral" problem: due to a functional impairment of the state of the microvessels with vascular rarefaction and destruction of the integrity of the vascular endothelium, leading to an abolition of reactional vasodilation and creating a real obstacle to tissue perfusion without any adaptive possibility. In this case, little or no central hypoperfusion is observed, but a direct effect on microcirculatory function, leading to peripheral hypoperfusion, is observed. This situation is encountered in cases of septic shock after initial hemodynamic treatment, but also in various pathological conditions where affected vascular reactivity and affected microcirculation are frequent and influence patient prognosis (for example in the case of diabetic patients, of patients with chronic hypertension, of patients suffering from system disease with angiitis, of patients suffering from renal failure, etc.).

These two situations can give the same quantitative evaluation of the impairment of microcirculatory perfusion (same elevation of tissue $CO_2$ and same decrease in PI), although they require fundamentally different therapies. In situation (1), termed "predominant central", an attempt will be made to rapidly restore central hemodynamics in a long-lasting manner, which will lead to a gradual improvement in microcirculatory perfusion. In situation (2), termed "predominant peripheral", the prognosis is more serious because of the structural damage to the microcirculation; etiological treatment is predominant and therapies specific to this situation are still currently being studied.

SUMMARY

The present invention provides a non-invasive method which makes it possible to distinguish the two situations described above, and therefore to provide the clinician with precious information regarding the condition of his patient. This method is based on the measurement of cutaneous $CO_2$ and/or PI during a hyperthermia challenge, in order to test the integrity of the microcirculation. A "hyperthermia challenge" is defined herein as a local and transient increase in the temperature of an area of the skin, preferably a richly vascularized area. For example, the skin of the area chosen can be brought to a temperature of between 40 and 48° C., for example 45° C., for a period of a few minutes. This makes it possible to test the capacity of the microcirculatory network to create a vasodilation induced by the increase in temperature. Schematically, this reactional vasodilation to hyperthermia will be present in a "predominant central"-type profile, attesting to a preservation of the properties of the vascular endothelium, and absent or weak in the "predominant peripheral" profile, owing to the destruction or the functional impairment of said vascular endothelium.

The present invention therefore relates, firstly, to a non-invasive method for testing the functionality of the vascular endothelium at the level of the microcirculatory network of a patient, comprising the following steps:
(i) measurements under normal temperature conditions: using one or more sensor(s) which are non-heated or maintained at a temperature of about 37° C. (chosen between 20° C. and 37° C., for example), the cutaneous $CO_2$ pressure ($P_cCO_2$) and the perfusion index (PI) of the patient are measured;
(ii) hyperthermia challenge: the sensor(s) is (are) then brought to a temperature chosen between 40° C. and 48° C., for example 45° C., and maintained at this temperature for a given period of about a few minutes (for example between 3 and 15 minutes), then brought back to its (their) initial temperature; during this challenge, the variations in the cutaneous $CO_2$ pressure and in the perfusion index of the patient are measured;
(iii) interpretation:
a drop in the cutaneous $CO_2$ pressure during the hyperthermia challenge, accompanied by a strong increase in the perfusion index (increase greater than a predetermined threshold), indicates that the vascular endothelium at the level of the microcirculatory network of the patient is functional;

an increase in the cutaneous $CO_2$ pressure during the hyperthermia challenge, accompanied by a moderate increase (less than a predetermined threshold) in the perfusion index, is indicative of the microcirculatory network of the patient being affected.

The variations in the cutaneous $CO_2$ pressure are, in the examples below, studied by calculating the difference $P_cCO_{2\ end} - P_cCO_{2\ start}$, denoted "$P_cCO_{2\ end-start}$". Of course, this variation can be evaluated by any other calculation from the values of the cutaneous $CO_2$ pressure measured during the test, capable of providing information on the variation in $P_cCO_2$. For example, it is possible to calculate the percentage of this variation in the following way: $(P_cCO_{2\ end} - P_cCO_{2\ start})/(P_cCO_{2\ end}$ or $P_cCO_{2\ start}) \times 100$.

According to a particular implementation of the method above, illustrated in the examples, the increase in the perfusion index is calculated as the ratio between the maximum and minimum values of this index during the complete test (including the measurements under normal temperature conditions). In practice, this amounts to calculating the ratio of the maximum value of the perfusion index during the hyperthermia challenge ($PI_{max}$) to its value under normal temperature conditions ($PI_{37°\ C.}$). This ratio will be denoted in what follows as "$PI_{max}/PI_{min}$". Of course, the variation in perfusion index can be measured by carrying out another calculation, for instance by calculating the difference $PI_{max} - PI_{min}$, either in net value or as a percentage $(PI_{max} - PI_{min})/(PI_{max}$ or $PI_{min}) \times 100$, or any other calculation based on the PI values which is capable of providing information on the variation in the perfusion index.

As illustrated below, the predetermined threshold for the interpretation of the increase in the perfusion index is preferably between 2 and 4.

In one preferred implementation of the invention, a single device integrates the $CO_2$ sensor and the sensor for measuring the perfusion index. This device will improperly be called in what follows "the sensor".

It is important to place the sensor in a richly vascularized area, in order to obtain reliable data on the tissue microcirculation. In a preferred implementation of the invention, the cutaneous $CO_2$ pressure and the perfusion index are therefore measured by a sensor placed on an earlobe.

An example of a material usable for implementing the method described above is the electrode of the Tosca® 500 (Radiometer®, Copenhagen) with the Masimo Set® technology. Indeed, this electrode makes it possible to measure the cutaneous $CO_2$ pressure in mmHg ($P_cCO_2$) at 37° C., with the proviso of dispensing with the automatic correction, as described in the article by Vallée et al. (Vallée et al., 2008) and in patent application WO 2011/024018, and to measure the perfusion index. In addition, the electrode of the Tosca 500 has an integrated device which makes it possible to heat the sensor up to 45° C. This technology was developed to create an intense vasodilation creating a tissue "arterialization", thus bringing together the cutaneous value of $PCO_2$ ($P_cCO_2$) and the arterial value ($P_aCO_2$), for monitoring of patients suffering from respiratory diseases.

According to one preferred implementation, the hyperthermia challenge is carried out in the following way: after stabilization of the $P_cCO_2$ value and of the PI at 37° C., the temperature of the sensor is increased to 45° C. for 5 min and then brought back down to 37° C. The variations in the value of $P_cCO_2$ and the PI are analyzed during this hyperthermia challenge and interpreted as described above and illustrated in the experimental section.

In addition to the variations in the $P_cCO_2$ and in the PI, other parameters can be measured during the implementation of the method according to the invention, and can provide additional information relating to the tissue perfusion state of the patient. In particular, it is possible to measure the time elapsed between the end of the hyperthermia challenge and the moment when the sensor again begins to consume energy in order to maintain its temperature at 37° C. (i.e. between 36.5 and 37.5° C.). This time, termed "reheating time", is linked to the quality of the tissue perfusion and to the fact that the vasodilation induced by the heating endures after the heating has stopped. Indeed, at stable ambient temperature, the power of the electric current required to heat the sensor at a constant temperature is dependent on the quality of the local tissue perfusion, the main source of heat for the skin tissue. Schematically, if the tissue perfusion is good, the monitor does not need to heat the sensor a great deal to maintain a constant temperature of 37° C., and vice versa. The skilled person in the art is able, by means of routine tests, to calibrate this parameter according to the various conditions under which the test is performed (room, ambient temperature, etc.), in order to interpret this parameter.

A variant of the above parameter is the energy consumed by the sensor in order to reach the temperature of 45° C. or in order to maintain its temperature at 37° C. for a predetermined period of time beginning at the end of the hyperthermia challenge. In the same way as for the previous parameter, if the tissue perfusion is good, the sensor will consume little energy in order to reach the temperature of 45° C. or to maintain a constant temperature of 37° C., and vice versa. This parameter may also be calibrated by means of routine measurements.

The monitoring of the $P_cCO_2$ coupled with the heating test enables evaluation and monitoring of the tissue perfusion state. The result of the test and the evolution thereof may make it possible to guide the therapy in various pathological conditions where tissue perfusion is impaired. An improvement in tissue perfusion will be noted by a drop in the basic $P_cCO_2$ value, and, on heating, a drop in the $P_cCO_2$ value during the test (drop in $P_cCO_{2\ end-start}$) and an increase in pulsatility (increase in $PI_{max}/PI_{min}$).

The method described above, in its different variants, is particularly useful in intensive care units, for determining the microcirculatory perfusion state of a patient in a state of shock, whether it is septic shock, hemorrhagic shock, allergic shock, cardiogenic shock, or the like.

Notably, this method provides new information which, in the context of a given clinical picture, helps the hospital practitioner in his prognosis for these patients, in particular for patients in septic shock, and helps him to give them better treatment. Indeed, the inventors have observed that, if the test described herein shows that the microcirculatory perfusion of the patient is good, this patient has a greater probability of surviving 28 days after the beginning of his shock than in the opposite case.

It is important to note that the method described herein is not limited to patients in a state of shock. On the contrary, it can be used to assist with the diagnosis, the prognosis and the treatment of patients exhibiting various symptoms and pathological conditions, where affected vascular reactivity and affected microcirculation are frequent and can influence patient prognosis and/or treatment. For patients exhibiting such symptoms and/or suffering from such pathological conditions, the method presented herein makes it possible to obtain information on the seriousness of the effect on tissue perfusion. This information adds to the clinical picture analyzed by the practitioner and thus constitutes an additional element for establishing a diagnosis and/or a prognosis and/or for adapting the patient's treatment. By way of nonlimiting examples of the situations in which the method of the invention can be advantageously used, mention may be made, in addition to the states of shock mentioned above, of diabetes, arteritis, including obliterative arteritis of the lower limbs, hypertension, system diseases with angiitis, renal failure, etc. The method according to the present invention is also useful for knowing the state of various tissues after a graft. By way of nonlimiting examples illustrating this application, mention may be made of musculocutaneous flaps for surgical reconstruction and the taking of a skin graft after a burn.

According to the clinical situations, the result of the test described herein will lead to a different treatment. For example, for a patient in septic shock, if the test described herein shows that the microcirculatory perfusion of the patient is weak (increase in the cutaneous $CO_2$ pressure during the hyperthermia challenge and/or increase less than a predetermined threshold in the perfusion index), a dose of vasoconstrictive medicament will be administered to the patient. Among the medicaments usable in this situation, mention may be made of vasopressin and analogs thereof, such as terlipressin, somatostatin and analogs thereof, among which are octerotide, dobutamine, epinephrine and norepinephrine, also called levarterenol or noradrenaline.

Conversely, a result of the test showing that the microcirculatory perfusion of a graft, for example a grafted flap, is weak will lead to the administration of a vasodilator and/or antiaggregating and/or anticoagulant treatment. By way of examples of vasodilator treatment administrable in this case, mention may be made of nitro derivatives (such as trinitrine, isosorbide dinitrate, molsidomine, nicorandil, etc.) and prostacyclin analogs (such as Iloprost), which can be administered locally, for example percutaneously (patch) or by injection, or systemically (orally or sublingually). The same type of treatment will be administered in other cases of local involvement in which the microcirculation is decreased, for instance in cases of obliterative arteriopathy of a limb (often a lower limb, obliterative arteritis of the lower limbs). In addition to or in place of such a treatment, the physician may decide to perform a revascularization by surgical thrombectomy or thrombolysis in situ.

Various applications of the method according to the present invention are mentioned below, by way of nonlimiting illustration:

1—During States of Shock (Septic, Cardiogenic, Hemorrhagic, allergic):
   Introduction, monitoring and withdrawal of a vasoconstrictor treatment of norepinephrine, epinephrine, vasopressin, dobutamine, etc., type: therapeutic decision taken according to the effect on tissue perfusion.
   Monitoring of the effect of vascular filling on tissue perfusion.

2—During Vascular Surgery and Reconstructive Surgery with Flaps
   Monitoring of tissue perfusion before and after vascular bypass, making it possible to test the viability and the effectiveness of the bypass, and to act accordingly (by administration of vasodilator, anticoagulant and/or antiaggregating medicaments, and/or surgical treatment).
   Monitoring of tissue perfusion before and after revascularization by the Fogarty technique (surgical thrombectomy) or thrombolysis in situ, or even thromboaspiration, making it possible to test the viability and the effectiveness of the revascularization procedure.
   Monitoring of the effect of anticoagulant medicaments of the heparin type, for adjustment of the dose administered if necessary.
   Monitoring of the effect of antiaggregating medicaments of the aspirin or antiGP2B3A type, for adjustment of the dose administered if necessary.
   Monitoring of the effect of vasodilator medicaments of the nitro derivative or prostacyclin analog (Iloprost) type, for adjustment of the dose administered if necessary.

3—During Obliterative Arteriopathy of the Lower Limbs in Particular in Diabetics
   Monitoring of the effect of the introduction of anticoagulant medicaments of the heparin or AVK type on tissue perfusion, for adjustment of the treatment if necessary.
   Monitoring of the effect of antiaggregating medicaments of the aspirin or antiGP2B3A type, for adjustment of the dose administered if necessary.
   Monitoring of the effect of medicaments of the statin type on atheroma, for adjustment of the dose administered if necessary.
   Monitoring of the effect of vasodilator medicaments of the nitro derivative, prostacyclin analog (Iloprost) or converting enzyme inhibitor (CEI) type, for adjustment of the dose administered or of the treatment if necessary.
   Monitoring of tissue perfusion before and after revascularization by the Fogarty technique (surgical thrombectomy) or thrombolysis in situ, or even thromboaspiration, making it possible to test the viability and the effectiveness of the revascularization procedure.
   Monitoring of the effect of a supervised training program for walking, for vascular rehabilitation of patients with obliterative arteritis of the lower limbs.

The present invention also relates to a device for carrying out a microcirculatory perfusion test as described above. Such a device comprises:
   a sensor for measuring the cutaneous $CO_2$ pressure ($P_cCO_2$);
   a sensor for measuring the pulsed oxygen saturation ($SpO_2$) of hemoglobin; preferably, these two sensors are integrated into one and the same object, for example suitable for the earlobe;
   for each sensor, means for heating and for controlling and measuring the temperature, capable of heating the sensor and maintaining its temperature at a chosen temperature (between 40° C. and 48° C.); the temperature range may be wider or narrower than the above-mentioned range. It is wider if the heating means are also used to maintain the sensor at a chosen temperature for the measurements under normal temperature conditions (which can be obtained by maintaining the sensor at a temperature between ambient temperature and 37° C.). If the measurements under normal temperature conditions are obtained without heating the sensor, the range of 40 to 48° C. may, on the contrary, be reduced, for example to between 44 and 46° C. The skilled person in the art will, according to economic criteria and the scope of the applications that they wish to give to the device according to the invention, choose appropriate means for heating and controlling the temperature;

computer means connected to the two sensors, making it possible to:

(i) program the change in temperature of the sensors for implementing the method (measurements under normal temperature conditions, hyperthermia challenge then return to 37° C.)

(ii) display and/or record the following parameters during the test:

the cutaneous $CO_2$ pressure (N.B.: this parameter should be presented without correction by a formula integrating the temperature of the sensor, or this correction should be canceled during the $P_cCO_2\ _{end-start}$ calculation step), and the perfusion index (PI);

(iii) calculate the difference in cutaneous $CO_2$ pressure between the end and the start of the hyperthermia challenge ($P_cCO_2\ _{end-start}$)/and also the ratio between the maximum and minimum values of the perfusion index during the test ($PI_{max}/PI_{min}$).

In one preferred embodiment of the device according to the invention, the computer means are also capable of displaying and/or recording the power delivered by the sensor during the test, and/or of calculating the energy consumed by the sensor during a predetermined period of time beginning at the end of the hyperthermia challenge.

BRIEF DESCRIPTION OF THE DRAWINGS

The following examples and figures illustrate the invention without, however, limiting its scope.

DETAILED DESCRIPTION

EXAMPLES

Example 1

Preliminary Study: Variations in the Cutaneous $CO_2$ Pressure ($P_cCO_2$) and in the Perfusion Index (PI) During a Hyperthermia Challenge in Order to Evaluate the Microcirculation in States of Shock 1.1. Materials and Methods Population Studied The study was carried out from December 2011 to September 2012 in the surgical intensive care unit of the Lariboisière hospital. All the patients in septic, cardiogenic or hemorrhagic shock that were hospitalized in our unit were included. Intensive care patients not suffering from shock were analyzed as controls, as were healthy volunteers. There was no modification of therapeutic treatment according to the results obtained from the hyperthermia tests. All the patients were treated according to the customary practices of the unit without taking into account the result of the test.

Measurement Protocols

The measurements were carried out after inclusion at less than 24 h from the beginning of the shock. At H0, H6, H12, H24, H36 and H48, all the clinical and biological data were collected and a dynamic hyperthermia test was carried out. The parameters collected at each time are temperature, hemodynamic data, arterial and venous blood gases (the venous blood came from an internal jugular catheter), arterial lactate, cardiac output, stroke volume, and end tidal $CO_2$ ($EtCO_2$). Each therapeutic treatment or measurement was recorded.

$P_cCO_2$ Measurements

The $P_cCO_2$ (mmHg) was measured on the earlobe with a Tosca 500 monitor (Tosca®, Radiometer Basel Ag; Basel, Basel-Stadt, Switzerland) at 37° C. without metabolic constant (technique described in application WO 2011/024018). The sensor was calibrated in vitro before use and then systematically every 12 hours. The sensor was then attached to a clip placed on the ear of the patient after application of a contact gel. Tosca 500 instrument, EC labeling No. 0037; material referenced at the APHP [Public Hospital System of the City of Paris and its suburbs].

Perfusion Index Measurements

The PI (%), a parameter which measures the proportion of signal pulsed in the obtaining of the $SpO_2$ signal, was measured using the Masimo technology (Masimo SET®). This technology is integrated into the electrode of the Tosca 500.

Hyperthermia Test

It was carried out at each time: H0, H6, H12, H24, H36 and H48, when the measurement of the $P_cCO_2$ at 37° C. was stable. The Tosca 500 monitor makes it possible to adjust the temperature of the electrode from 37° C. to 45° C. in steps of 0.5° C. The hyperthermia test consisted in heating the electrode at 45° for five minutes and then in returning it to 37°.

Statistical Analysis

The parameters of the heating test and the evolution thereof were compared as a function of the diagnosis of the patients and as a function of their outcome at D28 of hospitalization by repeated-measures ANOVA and a student's t test.

1.2. Results

Figure 1:
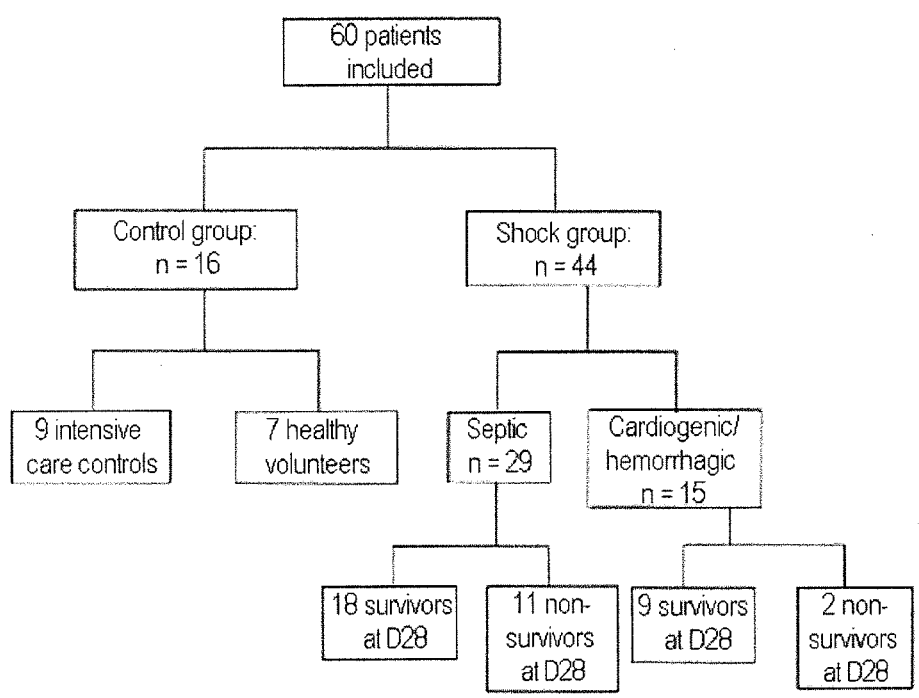
FIG. 1: flow chart of the preliminary study.

In total, 60 patients were included, divided up into three groups (FIG. 1).

Confirmation of the Results of the Study Described in Application WO 2011/024018

Figure 2:
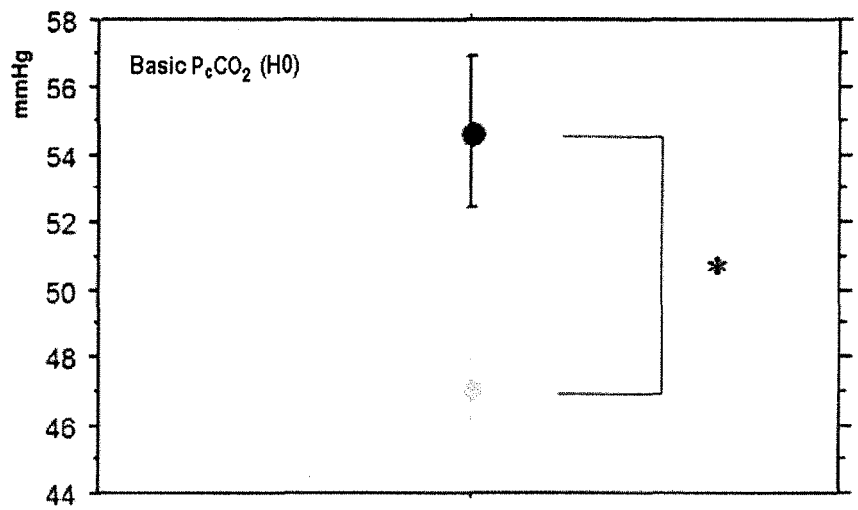
FIG. 2: comparison of the $P_cCO_2$ value of the patients suffering from shock (black) at the inclusion of the patients, compared with healthy controls (gray).

The patients suffering from shock have a significantly higher $P_cCO_2$ than the control patients (FIG. 2).

Figure 3:
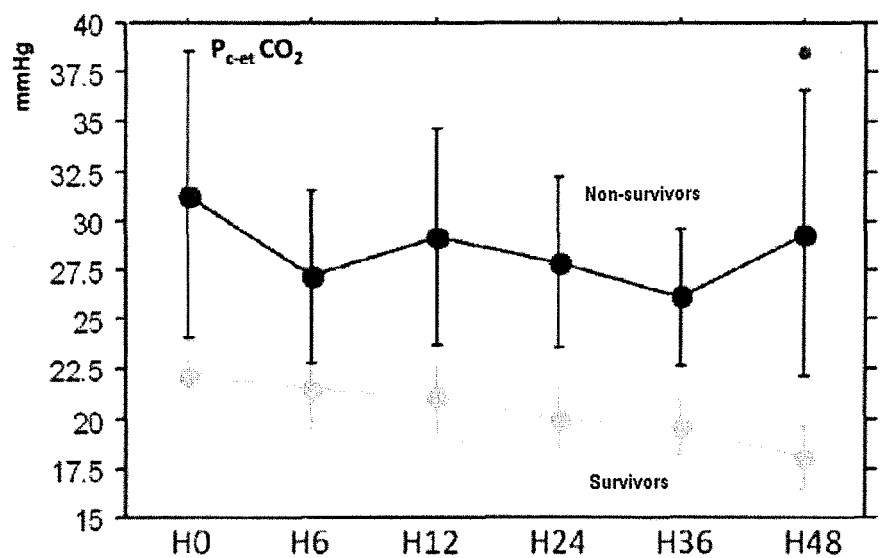
FIG. 3: comparison of the $P_cCO_2\ _{end-start}$ value at the inclusion of the patients.

During the first 48 hours of intensive care, the $P_{c-et}CO_2$ gradient of the patients who in the end survived (at 28 days) statistically dropped, contrary to the situation observed for the non-surviving patients (FIG. 3).

Figure 4:
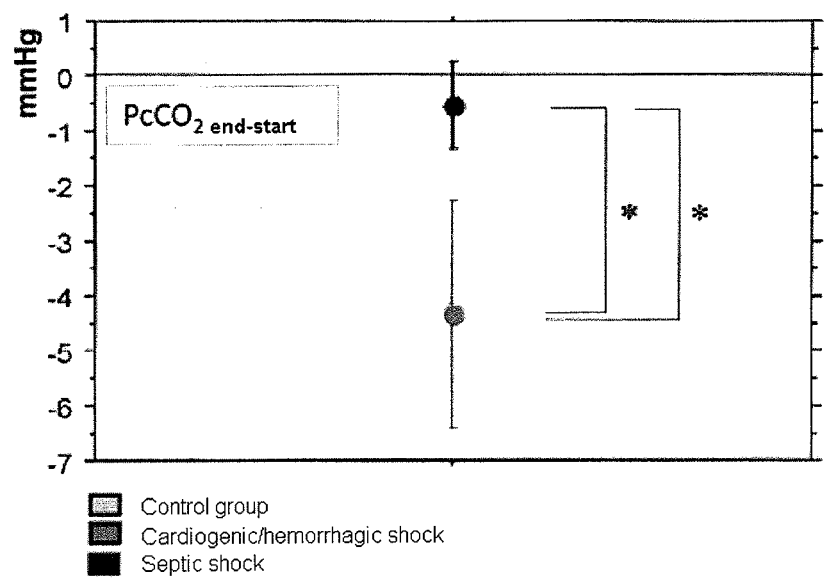
FIG. 4: evolution of the gradient $P_{c-Et}CO_2$ of the patients suffering from shock, during the 48 hours following their admission, as a function of their outcome.

Comparison of the $P_cCO_2$ $_{end-start}$ Value at the Inclusion of the Patients The patients of the control group, and also the patients of the cardiogenic/hemorrhagic shock group lower their $P_cCO_2$ significantly more during the hyperthermia test than the patients of the septic shock group:

$P_cCO_2$ $_{end-start}$=−4.25±3.28 compared with −0.55±4.31 mmHg, p<0.01, and $P_cCO_2$ $_{end-start}$=−4.33±8.01 compared with 0.55±4.31 mmHg, p=0.048, respectively (FIG. 4).

Comparison of the $PI_{max}/PI_{min}$ Ratio at the Inclusion of the Patients

Figure 5:
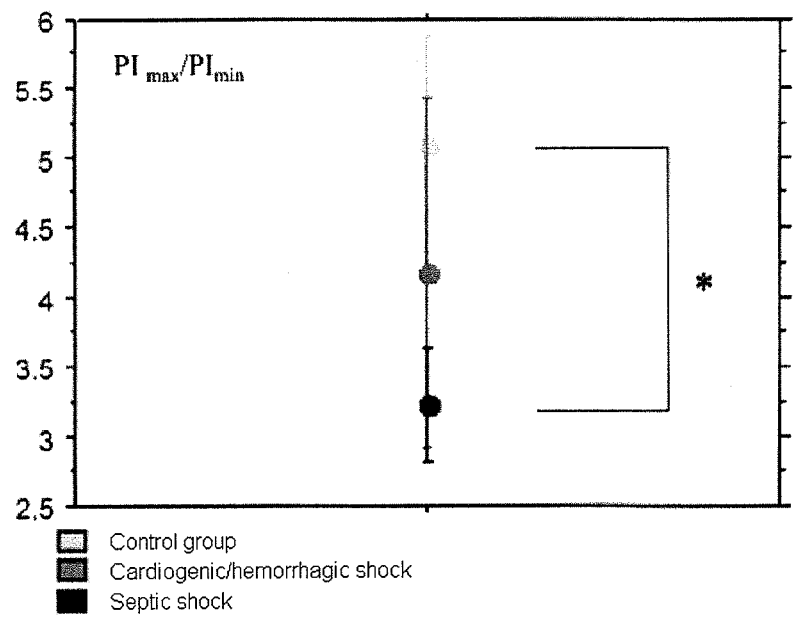
FIG. 5: comparison of the $PI_{max}/PI_{min}$ ratio at the inclusion of the patients.

During the heating test, the value of the PI is multiplied on average by 5 in the control group, by 4 in the cardiogenic/hemorrhagic group and by 3 in the septic group (FIG. 5). This difference is significant between the controls and the septic patients:

5.09±3.09 compared with 3.22±2.18, p=0.02.

Figure 6:
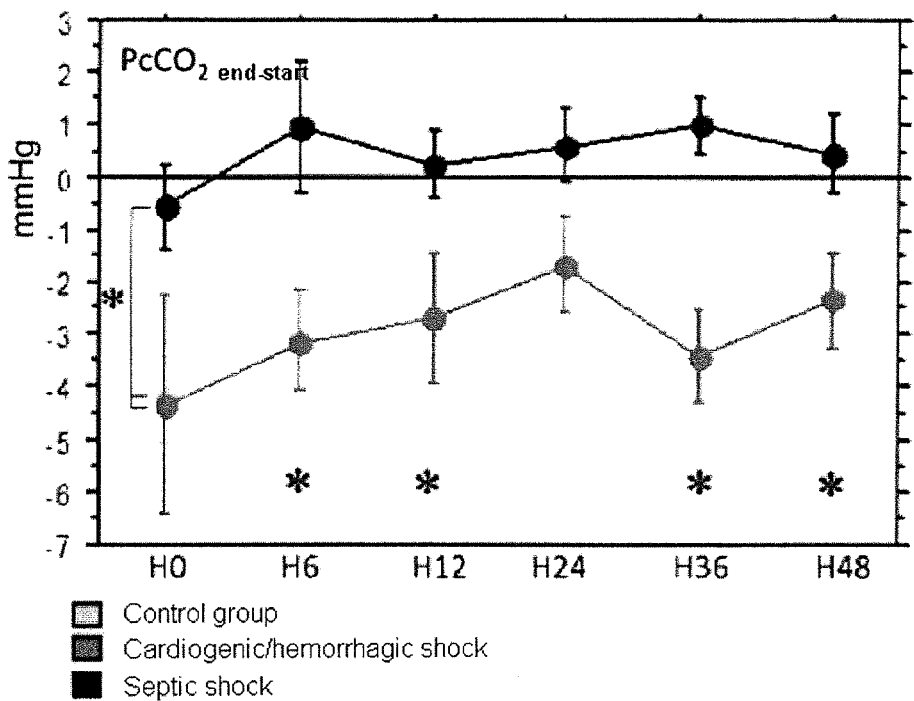
FIG. 6: evolution of $P_cCO_2\ _{end-start}$ during the first 48 h of intensive care as a function of patient diagnosis.

Evolution of $P_cCO_2$ $_{end-start}$ During the First 48 h of Intensive Care as a Function of Patient Diagnosis Starting from H6, the patients in septic shock increase their $P_cCO_2$ during the test (positive $P_cCO_2$ $_{end-start}$), whereas the patients in cardiogenic/hemorrhagic shock continue to lower the $P_cCO_2$ (FIG. 6). This difference is significant at H6, H12, H36 and H48.

Figure 7:
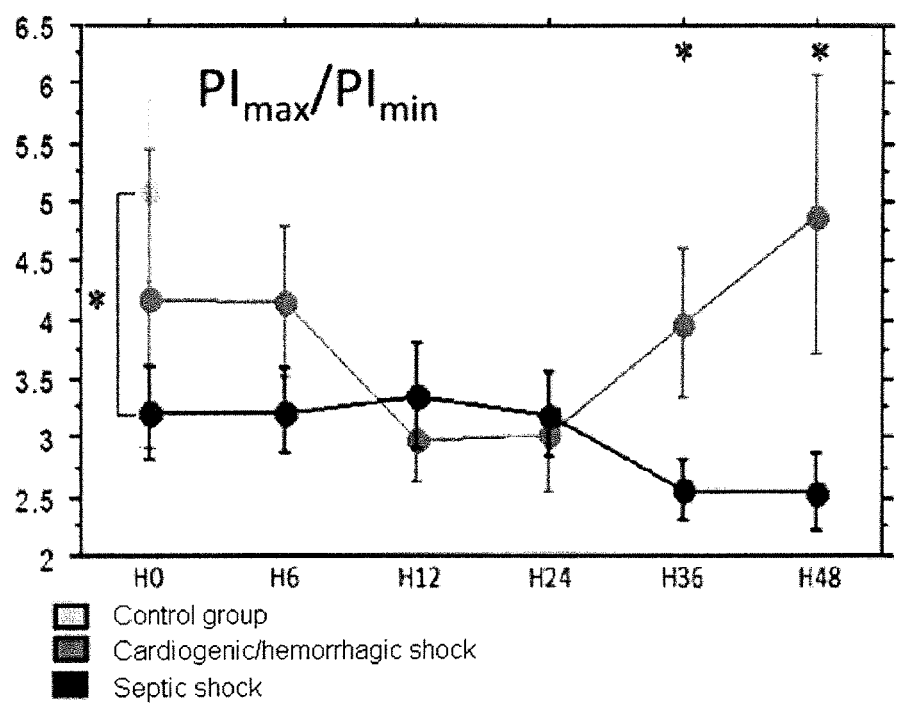
FIG. 7: evolution of the $PI_{max}/PI_{min}$ ratio during the first 48 h of intensive care as a function of patient diagnosis.

Evolution of the $PI_{max}/PI_{min}$ Ratio During the First 48 h of Intensive Care as a Function of Patient Diagnosis In the evolution of the first 48 h, a tendency to increase the $PI_{max}/PI_{min}$ ratio is seen in the cardiogenic/hemorrhagic group, contrary to the septic shock group (FIG. 7). At H48, the patients of the cardiogenic/hemorrhagic group return to a $PI_{max}/PI_{min}$ value close to that of the control patients at H0: 4.89±4.07 and 5.09±3.09. Furthermore, at H36 and at H48, the $PI_{max}/PI_{min}$ value in the patients of the cardiogenic/hemorrhagic group becomes significantly higher compared with the septic patients (3.97±2.19 compared with 2.56±1.21, p=0.02, and 4.89±4.07 compared with 2.53±1.34, p=0.03, respectively).

Evolution of $P_cCO_2$ $_{end-start}$ During the First 48 h of Intensive Care as a Function of Patient Prognosis (Mortality at D28)

Figure 8:
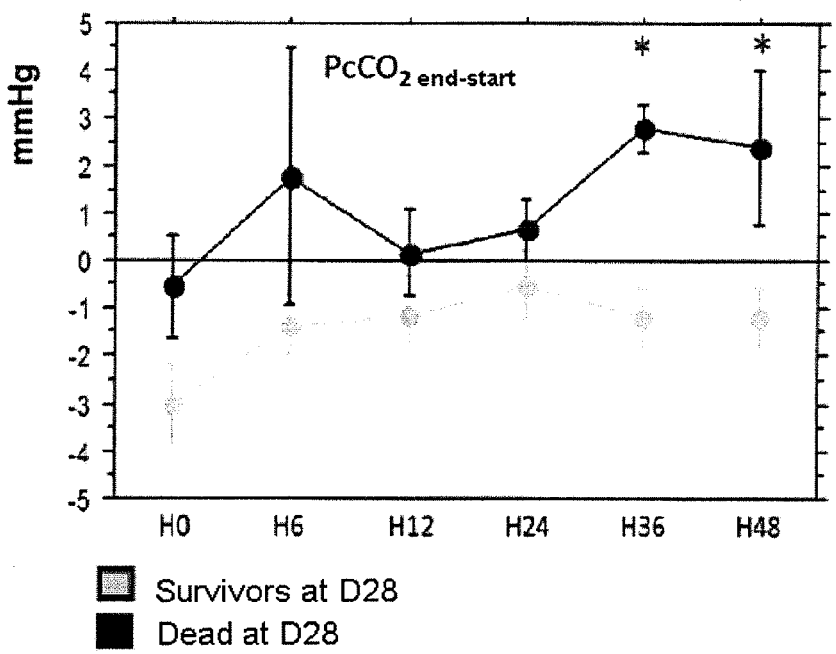
FIG. 8: evolution of $P_cCO_2\ _{end-start}$ during the first 48 h of intensive care as a function of patient prognosis (mortality at D28).

Starting from H6, the non-survivors increase their $P_cCO_2$ during the hyperthermia challenge (positive $P_cCO_2$ $_{end-start}$), whereas the survivors systematically lower it (negative $P_cCO_2$ $_{end-start}$) during the first 48 hours (FIG. 8). This difference is significant at H36 and H48:

$P_cCO_2$ $_{end-start}$=2.80±1.10 compared with −1.21±3.34 mmHg, p=0.01, and $P_cCO_2$ $_{end-start}$=2.40±3.65 compared with −1.19±3.16, p=0.03, respectively.

Evolution of $PI_{max}/PI_{min}$ During the First 48 h of Intensive Care as a Function of Patient Prognosis (Mortality at D28)

Figure 9:
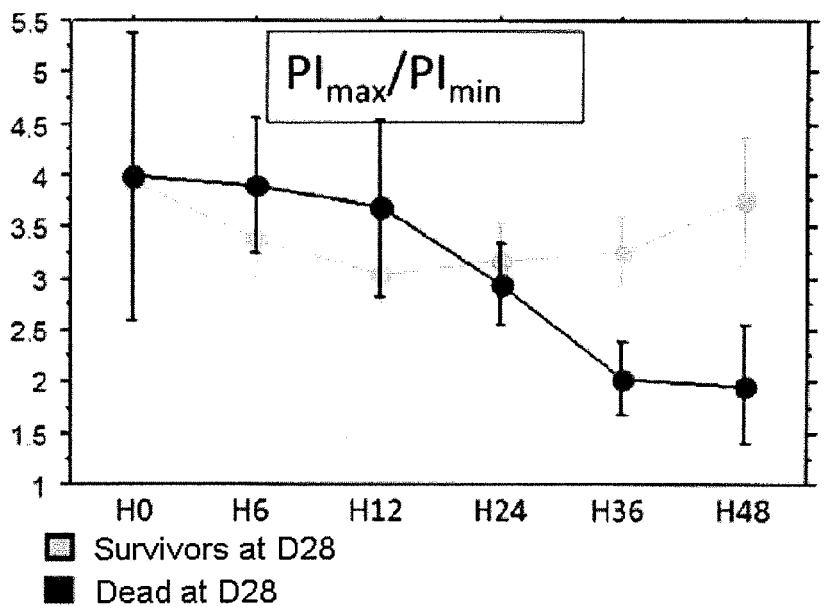
FIG. 9: evolution of $PI_{max}/PI_{min}$ during the first 48 h of intensive care as a function of patient prognosis (mortality at D28).

Contrary to the survivors, the non-survivors significantly lower their $PI_{max}/PI_{min}$ ratio during the first 36 hours: from 3.99±5.05 to 1.97±1.14, p=0.03 (FIG. 9). The $PI_{max}/PI_{min}$ of the non-survivors is significantly lower than the survivors at H48: 1.97±1.14 compared with 3.76±3.13, p=0.10. Furthermore, the evolution of the $PI_{max}/PI_{min}$ during the first 48 h is significantly different between the survivors and non-survivors, p=0.02 (§: p<0.05 with repeated-measures ANOVA).

1.3. Discussion

The results of this study confirm the results presented in application WO 2011/024018:

1—The patients in states of shock have a $P_cCO_2$ at 37° C. that is higher than the control patients.

2—The survivors lower their $P_{c-Et}CO_2$ gradient in the first 48 hours compared with the non-survivors.

In addition, these results show that, during a hyperthermia challenge:

1—The patients in whom the microcirculatory perfusion is not functionally affected (control patients and the patients in cardiogenic or hemorrhagic shock) lower their cutaneous $CO_2$ ($P_cCO_2$ $_{end-start}$=−4 mmHg on average) at H0. This drop is also found during the first 48 hours for the patients in cardiogenic or hemorrhagic shock.

2—The patients in cardiogenic or hemorrhagic shock at 48 h of treatment return to a pulsatility ($PI_{max}/PI_{min}$) identical to the control patients.

3—The patients in septic shock, in whom the microcirculatory perfusion is more seriously functionally affected, and in whom there is endothelial dysfunction, have different results in the hyperthermia test since they increase overall their $P_cCO_2$ during the test (positive $P_cCO_2$ $_{end-start}$) and have a reduced pulsatile response to hyperthermia (low $PI_{max}/PI_{min}$).

4—This response to the hyperthermia test is linked to the prognosis: in the first 48 hours, the patients who will survive always have a decrease in their $P_cCO_2$ during the hyperthermia challenge, with gradual restoring of pulsatility (increase in the $PI_{max}/PI_{min}$).

1.4. Conclusion

The test described herein, with hyperthermia challenge in addition to the analysis of cutaneous $CO_2$ at 37° C., makes it possible to test the integrity of the endothelial and microcirculatory function during states of shock, namely:

negative $P_cCO_2$ $_{end-start}$ the heating of the sensor leads to vasodilation which makes it possible to eliminate the $CO_2$ produced by the tissue;

high $PI_{max}/PI_{min}$ (>3): the heating of the sensor increases the pulsatility of the tissue perfusion.

These results show that a poor response to the hyperthermia test (positive $P_cCO_2$ $_{end-start}$ and low $PI_{max}/PI_{min}$ (<2)) confirms that the endothelial and microcirculatory function has been affected during the state of shock and influences patient prognosis.

Example 2

Microcirculatory Perfusion Test Integrating a Hyperthermia Challenge 2.1. Description of the Test The basic $P_cCO_2$ is the measurement of the $P_cCO_2$ before beginning the hyperthermia challenge, when the sensor is at 37° C.

Figure 10:
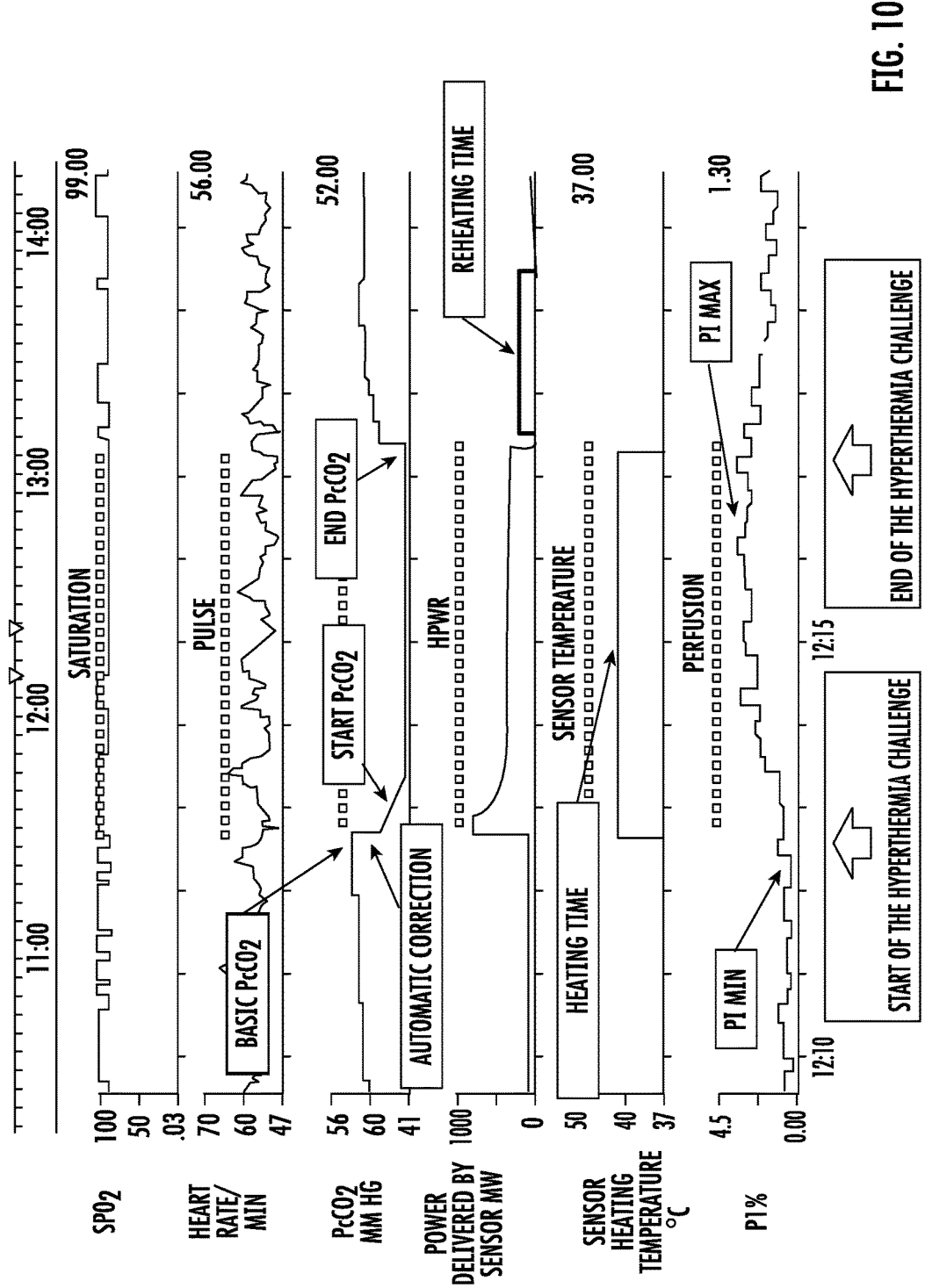
FIG. 10: descriptive diagram of the test according to the invention.

The parameters calculated with the data from the test are illustrated in FIG. 10. They are:

$P_cCO_2$ $_{end-start}$: this is the difference between the value of the $P_cCO_2$ after five minutes of heating of the sensor at 45° C. and the initial value at 37° C. In practice, when the instrument used makes an automatic correction, the initial value ($P_cCO_2$ start) is taken to be the value of the $P_cCO_2$ immediately after the start of the heating, when the automatic correction has integrated the change in temperature of the sensor but the heating has not yet had an impact on the value of the cutaneous $CO_2$ pressure.

N.B.: the automatic correction systematically lowers the value of the $P_cCO_2$ displayed as a function of the increase in the temperature according to the following relationship: $P_cCO_2$ displayed=$P_{tc}CO_2$ measured/$10^{(0.019 \times (T°-37))}$, where T° is the temperature of the sensor (Severinghaus et al., transcutaneous blood gas analysis. *Respiratory Care*, 1982, Hazinski and Severinghaus, 1982).

$PI_{max}/PI_{min}$ is the ratio between the highest PI value ($PI_{max}$) during the hyperthermia challenge and the lowest PI value ($PI_{min}$) during the whole of the test (including the measurement before the hyperthermia challenge and, in certain cases, a period of time after the hyperthermia challenge has been stopped). In practice, $PI_{min}$=PI at 37° C., before the heating test.

The "reheating time": this parameter corresponds to the time, expressed in seconds, starting from which the sensor begins to reheat the skin in order to obtain a temperature of 37° C. after the hyperthermia challenge.

2.2. Standard Test: "Predominant Central" Problem

Figure 11:
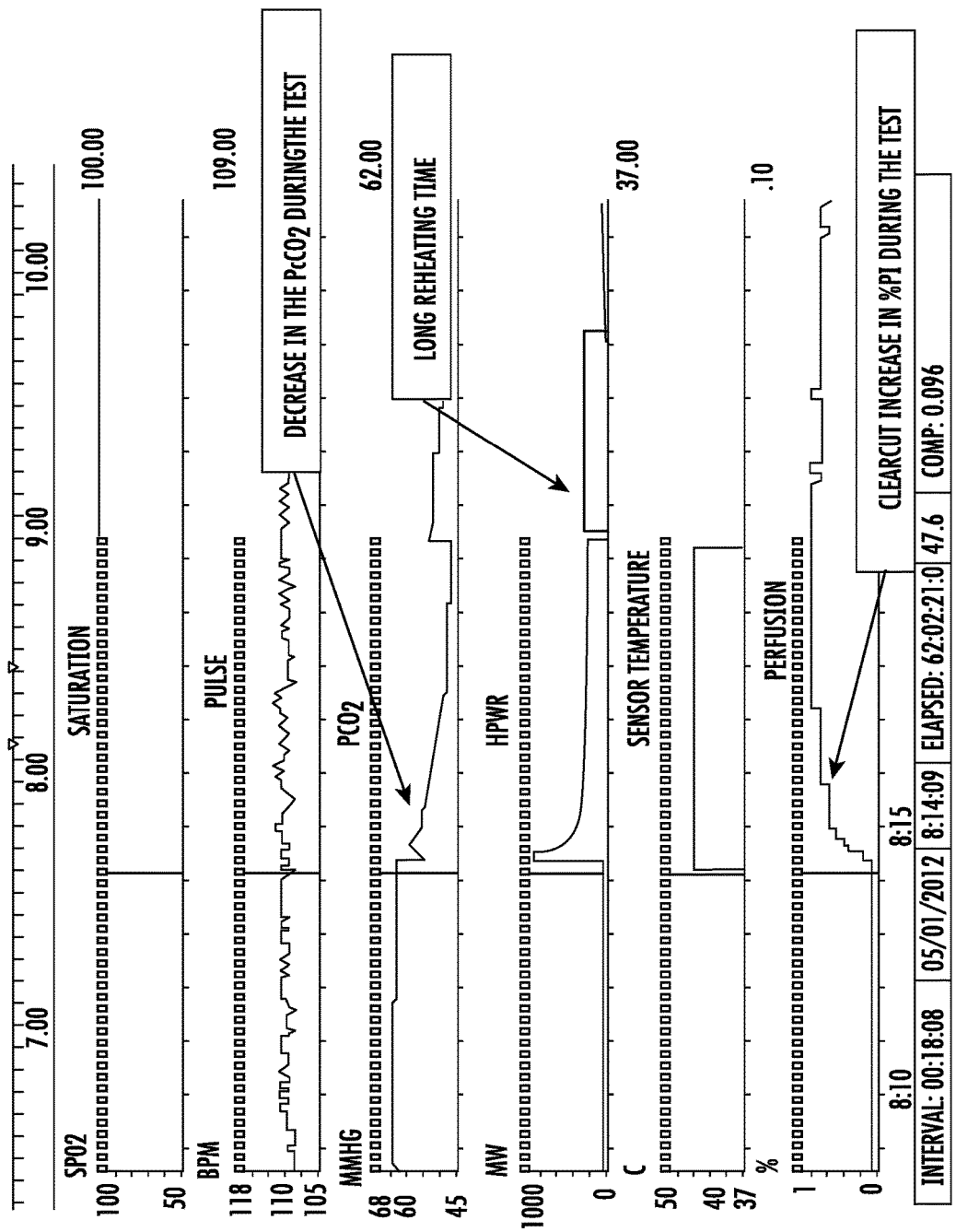
FIG. 11: data typically obtained during the test, for a patient not exhibiting any functional effect on the vascular endothelium at the level of the microcirculatory network ("predominant central" profile).
Figure 12:
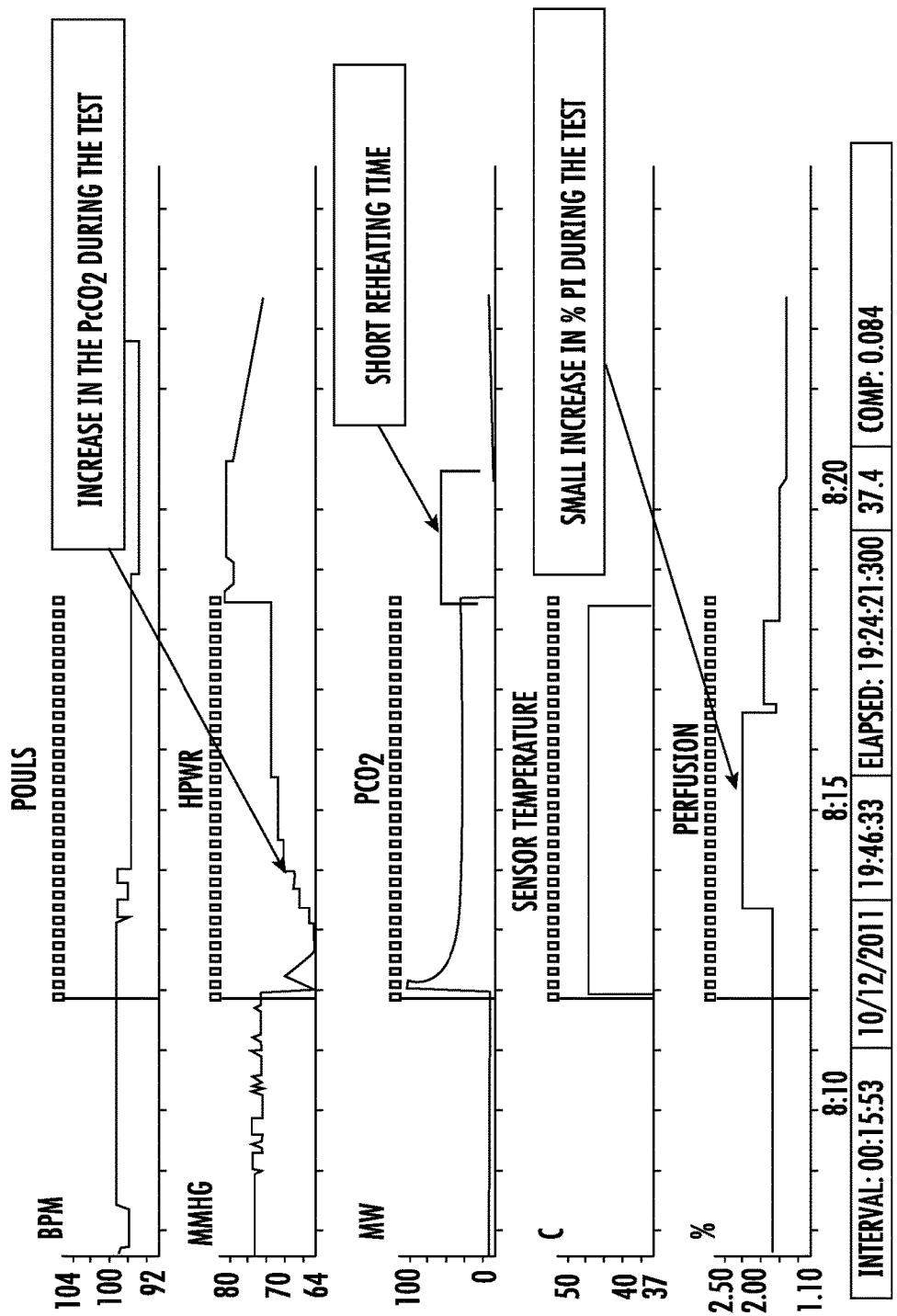
FIG. 12: data typically obtained during the test, for a patient exhibiting a functional effect on the vascular endothelium at the level of the microcirculatory network ("predominant peripheral" profile).

FIG. 11 illustrates the data typically obtained during the test according to the invention, for a patient in whom the vascular endothelium at the level of the microcirculatory network is not functionally affected.

The vasodilation induced by the heating made it possible to increase the tissue perfusion flow and the pulsatility, causing the $CO_2$ produced by the tissues to be rinsed away. The microcirculation is not functionally affected, since there is a vasodilation induced by the heating. Furthermore, this reactional vasodilation is long-lasting since the instrument does not need to rapidly reheat the sensor in order to obtain a stable temperature of 37° C. The profile is therefore a "predominant central" profile. The therapy will consist in restoring and maintaining the central hemodynamics and monitoring the return to normal of the peripheral tissue perfusion with a return to normal of the value of the $P_cCO_2$ and of the PI.

2.3. Standard Test: "Predominant Peripheral" Problem

The $P_cCO_2$ value increases (positive $P_cCO_2$ $_{end-start}$), the PI changes little or not at all ($PI_{max}/PI_{min}$<2) and the sensor reheating time is short: the profile is definitely a "predominant peripheral" profile. The $CO_2$ produced by the heating to 45° C. is not rinsed away and accumulates in the tissue. The heating causes no (or little) vasodilation nor increase in pulsatility and in microcirculatory perfusion. The monitor has to rapidly reheat after the end of the test in order to maintain a constant sensor temperature. This demonstrates the functional impairment of the microcirculation with dysfunction of the properties of the vascular endothelium. The prognosis is more serious than in the previous case.

2.4. Conclusion

The hyperthermia challenge is therefore a supplement to the analysis of the $P_cCO_2$ under normal temperature conditions on the earlobe (application WO 2011/024018): an increase in the $P_cCO_2$ reveals an abnormality of the microcirculatory perfusion and the hyperthermia test, coupling an analysis of the $P_cCO_2$, of the PI and, where appropriate, of the reheating time, makes it possible to classify this abnormality and to test the integrity of the microcirculatory network. This non-invasive test with no discomfort for the patient tests the functionality of the vascular endothelium by monitoring the amplitude of the vasodilation induced by the increase in temperature. It provides information on the seriousness of the effect on the microcirculation and can make it possible to orient the therapy.

Example 3

Examples of Patient Progression According to Pathological Condition and Prognosis 3.1. Intensive Care Control Patient The test on an intensive care control patient shows that said patient has no microcirculation abnormality. The $P_cCO_2$ value decreases by −5 mmHg during the hyperthermia challenge. The $PI_{max}/PI_{min}$ ratio at 7.5 itself also shows preserved microcirculation reactivity, with increase in pulsatility. The reheating time is greater than 200 seconds (table 1).

TABLE 1

|  | H0 |
|---|---|
| $P_cCO_2$ $_{end-start}$ | −5 |
| $PI_{max}/PI_{min}$ | 7.5 |
| Reheating time (s) | 222 |

3.2. Patient in Hemorrhagic Shock with Good Prognosis

The heating test on a patient in hemorrhagic shock during intensive care shows that there is a microcirculatory reactivity since there is a decrease in the $P_cCO_2$ $_{end-start}$ over time, with a $PI_{max}/PI_{min}$ ratio always greater than 4 and a long reheating time which extends over time (table 2).

TABLE 2

|  | H0 | H6 | H12 | H24 | H36 | H48 |
|---|---|---|---|---|---|---|
| $P_cCO_2$ $_{end-start}$ | −14 | −4 | −6 | −6 | −5 | −4 |
| $PI_{max}/PI_{min}$ | 6 | 4.2 | 7 | 9 | 6 | 5.8 |
| Reheating time (s) | 127 | 120 | 153 | 192 | 109 | 176 |

3.3. Patient in Cardiogenic Shock with Good Prognosis

In this patient in cardiogenic shock, the hyperthermia challenge shows that there is good vascular reactivity, which leads to efficient rinsing out of the tissue $CO_2$, hence a $P_cCO_2$ $_{end-start}$ value which is always negative. The $PI_{max}/PI_{min}$ value is itself always high and the reheating time increases over time (table 3).

TABLE 3

|  | H0 | H6 | H12 | H24 | H36 | H48 |
|---|---|---|---|---|---|---|
| $P_cCO_2$ $_{end-start}$ | −22 | −14 | −12 | −3 | −7 | −8 |
| $PI_{max}/PI_{min}$ | 5 | 2.3 | 5 | 5 | 8 | 13 |
| Reheating time (s) | 130 | 152 | 229 | 207 | 216 | 214 |

3.4. Septic Patient with Good Prognosis

In this patient in septic shock, the hyperthermia challenge shows that there is a conserved vascular reactivity which makes it possible to cause the $P_cCO_2$ end–start value to decrease and to cause the $PI_{max}/PI_{min}$ ratio to increase. The reheating time is itself also relatively long. The microcirculation is not therefore functionally affected (table 4).

TABLE 4

|  | H0 | H6 | H12 | H24 | H36 | H48 |
|---|---|---|---|---|---|---|
| $P_cCO_2\ _{end-start}$ | 0 | −5 | −6 | −2 | −4 | −3 |
| $PI_{max}/PI_{min}$ | 2.3 | 4 | 2.4 | 6.25 | 4.2 | 3.6 |
| Reheating time (s) | 247 | 207 | 208 | 169 | 179 | 193 |

3.5. Septic Patient with Poor Prognosis

This is a patient in septic shock due to peritonitis who died on D1 from multiple organ failure. During the hyperthermia challenges, the $P_cCO_2$ value increases (positive $P_cCO_2\ _{end-start}$) the PI value increases only slightly ($PI_{max}/PI_{min}$<2) and the reheating time is very short (table 5).

TABLE 5

|  | H0 | H6 | H12 | H24 |
|---|---|---|---|---|
| $P_cCO_2\ _{end-start}$ | +6 | 0 | +3 | +4 |
| $PI_{max}/PI_{min}$ | 1.5 | 1.3 | 1.1 | 1.1 |
| Reheating time (s) | 103 | 74 | 78 | 91 |

3.6. Patient after Reconstructive Surgery

A 42-year-old patient operated on for an ENT tumor with reconstruction using a free flap of latissimus dorsi. Continuous monitoring of the $P_cCO_2$ and of the PI on the flap during the first three post-operative days. Heating test carried out every 12 hours and clinical monitoring of the viability of the flap.

In this type of surgery, the viability of a free flap is a major question for the surgeon post-operatively. The monitoring of the $P_cCO_2$ with heating test can provide information on the perfusion of the flap and its viability.

Result: a gradual drop in the statistical $P_cCO_2$ values and, during the heating tests, a greater drop over time in the $P_cCO_2$ value during the hyperthermia challenge ($P_cCO_2\ _{end-start}$ going from 0 to −5 mmHg from H0 to H48) and an increase in the pulsatility on heating ($PI_{max/min}$ from 0 to +5) are noted. This demonstrates an improvement in the tissue perfusion of the flap, which was confirmed clinically by the good medium-term viability of the flap.

TABLE 6

|  | H0 | H12 | H24 | H36 | H48 | H60 | H72 |
|---|---|---|---|---|---|---|---|
| $P_cCO_2$ mmHg | 72 | 68 | 60 | 55 | 52 | 50 | 50 |
| % PI | 0 | 0.2 | 0.3 | 0.2 | 0.1 | 0.3 | 0.6 |
| $P_cCO_2\ _{end-start}$ mmHg | 0 | 0 | −1 | −5.2 | −5.4 | −4.7 | −4.9 |
| $PI_{max/min}$ | 0 | 2.2 | 3.3 | 3.5 | 4.1 | 4.2 | 5.6 |

Conclusion: this example shows the great advantage of the measurement of the $P_cCO_2$ and of the heating tests in the context of surgery with vascular bypass. The measurement also makes it possible to optimize the vasoactive treatments used in these situations (vasodilator medicaments, such as nitro derivatives).

3.7. Arteriopathy of the Lower Limbs in Patients Suffering from Arteritis and Diabetes A 65-year-old diabetic patient with hypertension, admitted to intensive care following abdominal surgery of the gall bladder. Upon the patient's arrival, an asymmetry of the coloration of the legs is noted: the right leg is paler, with a weak peripheral pulse compared with the left leg.

The comparative measurement of the $P_cCO_2$ with heating test was carried out in this clinical case in order to verify that the test of the invention can provide information on the vascular damage in patients suffering from arteritis.

Result: an asymmetry of the statistical $P_cCO_2$ values was observed, and also a poor reactivity to heating of the right leg. An angioscan confirmed the diagnosis of acute ischemia of the right lower limb, and revascularization was performed on the patient using the Fogarty technique (Fogarty catheter embolectomy). Post-operatively, the $P_cCO_2$ value redescended to normal values in the right leg with good reactivity to heating.

TABLE 7

|  | Left leg Pre-Op | Left leg Post-Op | Right leg Pre-Op | Right leg Post-Op |
|---|---|---|---|---|
| $P_cCO_2$ mmHg | 48 | 47 | 88 | 55 |
| % PI | 1.4 | 1.8 | 0 | 0.8 |
| $P_cCO_2\ _{end-start}$ mmHg | −3.8 | −4.1 | +3 | −5 |
| $PI_{max/min}$ | 4.2 | 3.7 | 0 | 4.2 |

Conclusion: this example shows the great advantage of the measurement of the $P_cCO_2$ and of the heating tests in a patient suffering from arteritis, who is in particular diabetic, for monitoring lower limb vascularization. The $P_cCO_2$ measurement and the heating test also make it possible to optimize the vasoactive treatments used in these situations.

REFERENCES

Severinghaus et al., transcutaneous blood gas analysis. Respiratory Care, 1982.

Hazinski, T. A. and Severinghaus, J. W. (1982) Transcutaneous analysis of arterial $PCO_2$. Med Instrum, 16, 150-153.

Vallèe, F., Vallet, B., Mathe, O., Parraguette, J., Mari, A., Silva, S., Samii, K., Fourcade, O. and Genestal, M. (2008) Central venous-to-arterial carbon dioxide difference: an additional target for goal-directed therapy in septic shock? Intensive Care Med, 34, 2218-2225.

Vallèe F, Mateo J, Dubreuil G, Poussant T, Tachon G, Ouanounou I, Payen D. (2010) Cutaneous ear lobe $PCO_2$ at 37° C. to evaluate microperfusion in patients with septic shock. Chest. 2010 November; 138(5): 1062-70, doi: 10.1378/chest.09-2690. Epub 2010 May 14.

The invention claimed is:

1. A non-invasive method for determining the microcirculatory perfusion state of a patient, comprising the following steps:
    carrying out the following measurements:
        measuring of cutaneous $CO_2$ pressure ($PcCO_2$) of the patient;
        measuring of perfusion index (PI) of the patient;
    wherein said measurements are carried out using one or more sensor(s) which are maintained at an initial temperature chosen between 30° C. and 37° C. or of a non-heated, ambient temperature,
        performing a hyperthermia challenge consisting of: starting with increasing the temperature of the sensor(s) from said initial temperature to a heating temperature chosen between 40° C. and 48° C.; maintaining said sensor(s) at said heating temperature for a period of between 3 and 15 minutes, and bringing the temperature of the sensor(s) to said initial temperature, wherein said hyperthermia challenge ends when the temperature of the sensor(s) have recovered said initial temperature, and measuring a $PcCO_{2\_start}$, wherein $PcCO_{2\_start}$ is the cutaneous $CO_2$ pressure at a start of said hyperthermia challenge:

measuring a $PcCO_{2\_heated}$, wherein $PcCO_{2\_heated}$ is the cutaneous $CO_2$ pressure at five minutes into said heating temperature of said hyperthermia challenge;

determining a $PcCO_{2\_heated-start}$ by calculating a difference $PcCO_{2\_heated} - PcCO_{2\_start}$;

measuring the perfusion index of the patient during said hyperthermia challenge, and determining a maximum value of the perfusion index obtained during said hyperthermia challenge;

interpreting the functionality of vascular endothelium at the level of the microcirculatory network;

indicating that the vascular endothelium at the level of the microcirculatory network of the patient is functional when $PcCO_{2\_heated-start}$ is a non-positive value, accompanied by a ratio between the maximum value of the perfusion index obtained during said hyperthermia challenge and the perfusion index (PI) of the patient at said initial temperature being greater than a predetermined threshold of between 2 and 4; and indicating that the microcirculatory network of the patient is affected when $PcCO_{2\_heated-start}$ is a positive value, accompanied by a ratio between the maximum value of the perfusion index obtained during said hyperthermia challenge and the perfusion index (PI) of the patient at said initial temperature being lesser than a predetermined threshold of between 2 and 4.

2. The method as claimed in claim 1, wherein the cutaneous $CO_2$ pressure and the perfusion index are measured by a sensor placed on an earlobe.

3. The method as claimed in claim 1, further comprising the measurement of the time elapsed between the end of the hyperthermia challenge and the moment when the sensor again begins to consume energy in order to maintain its temperature at 37° C.

4. The method as claimed in claim 1, further comprising the measurement of the energy consumed by the sensor in order to increase the temperature thereof to the temperature chosen for the hyperthermia challenge or to maintain its temperature at 37° C. for a predetermined period of time beginning at the end of the hyperthermia challenge.

5. The method of claim 1, further comprising: obtaining information relating to the prognosis for the chances of survival at 28 days for a patient in a state of shock by determining the microcirculatory perfusion state of the patient and interpreting the indication of the vascular endothelium at the level of the microcirculatory network being functional as a good prognosis for this patient or the indication of the microcirculatory network of the patient being affected as a poor prognosis.

* * * * *